United States Patent

Sundström et al.

Patent Number: 5,913,849
Date of Patent: Jun. 22, 1999

[54] HEAT DRESSING

[75] Inventors: Staffan Sundström, Helsingborg, Sweden; Lars Schønfeldt, Helsingør; Peter Boman Samuelsen, Kyst, both of Denmark

[73] Assignee: Coloplast A/S, Denmark

[21] Appl. No.: 08/743,999

[22] Filed: Nov. 4, 1996

Related U.S. Application Data

[63] Continuation of application No. 08/307,750, filed as application No. PCT/DK93/00115, Mar. 26, 1993.

[30] Foreign Application Priority Data

Mar. 27, 1992 [SE] Sweden .................................. 0409/92

[51] Int. Cl.$^6$ ........................................................ A61F 7/00
[52] U.S. Cl. ................................ 604/291; 602/2; 602/56; 602/57; 607/2; 607/96
[58] Field of Search .................... 602/2, 54, 57, 602/42, 43, 48, 52, 56; 607/2, 96, 98; 604/291

[56] References Cited

U.S. PATENT DOCUMENTS

| | | |
|---|---|---|
| Re. 22,763 | 6/1946 | Clark . |
| 2,590,212 | 3/1952 | Samuels . |
| 3,096,428 | 7/1963 | Dublirer et al. . |
| 3,202,801 | 8/1965 | Saluri . |
| 3,687,143 | 8/1972 | Schneeberger et al. ................ 128/402 |
| 3,867,939 | 2/1975 | Moore et al. ............................ 128/254 |
| 4,142,521 | 3/1979 | Konikoff ................................. 128/82.1 |
| 4,474,570 | 10/1984 | Ariura et al. ............................. 604/20 |
| 4,619,252 | 10/1986 | Ibbott ..................................... 128/82.1 |
| 4,699,146 | 10/1987 | Sieverding .............................. 128/640 |
| 4,722,354 | 2/1988 | Axelgaard et al. ..................... 128/798 |
| 4,743,499 | 5/1988 | Valke .................................... 428/317.3 |
| 4,767,401 | 8/1988 | Seiderman ................................ 604/20 |
| 4,817,594 | 4/1989 | Juhasz ................................... 128/155 |
| 4,909,244 | 3/1990 | Quarfoot et al. ...................... 128/156 |
| 4,982,742 | 1/1991 | Claude ................................... 128/798 |
| 5,218,973 | 6/1993 | Weaver et al. ......................... 128/798 |
| 5,419,913 | 5/1995 | Podell et al. ........................... 424/448 |

*Primary Examiner*—Corrine McDermott
*Assistant Examiner*—Cris L. Rodriguez
*Attorney, Agent, or Firm*—Ostrolenk, Faber, Gerb & Soffen, LLP

[57] ABSTRACT

A heat dressing for treatment of skin areas and comprising a heat generating unit and a liquid-absorbing adhesive layer which prior to use is coated with a strippable release layer. The adhesive layer is preferably of a hydrocolloidal material and may optionally contain one or more medicaments or be coated with alginate fibre mats. The heat generating unit generates heat preferably by means of galvanic or chemical energy, and the heat dressing may further comprise elements for controlling the heat development and/or the surface temperature.

13 Claims, 3 Drawing Sheets

HEAT DRESSING

This is a continuation of application Ser. No. 08/307,750 filed Sep. 26, 1994, and now U.S. Pat. No. 5,662,624 which was the National Stage of International Application No. PCT/DK 93/00115 filed Mar. 26, 1993.

BACKGROUND OF THE INVENTION

The present invention relates to a self-adhesive heat dressing for use in local treatment of skin and body areas.

Heat is widely used for treatment of minor nuisances, such as infiltrations and muscular tensions.

In most cases, the heat treatment is capable of removing or minimizing these nuisances by a relatively short treatment. Heat is also used as an analgesic e.g. for menstrual pain. Heat treatment is particularly important for treatment of rheumatism. Rheumatism cannot be cured, but the heat treatment can ease the worst pain.

Heat treatment has also been found to have significant effect for reducing skin lesions, such as e.g. psoriasis plaques. An article by Harukuni Urabe, MD, Keiko Mishitani, MD, Hiromu Konda, MD: Hyperthermia in the Treatment of Psoriasis. Arch. Dermatol.—Vol. 117, December 1981, pp. 770–774, mentions an experiment in which psoriasis has successfully been treated with heat.

The treatment lasted for 13–53 days. The heat dressing was changed 2–3 times a day, and in each period the skin temperature was raised to between 42 and 43° C., which temperature was maintained for more than 2 hours.

For many years it has been known that the temperature is of great importance for regeneration of tissue, and thus also for the healing process in a wound area. In particular, attention has been given to the fact that a lowered temperature in a wounded area causes reduced metabolism and consequently reduced wound-healing. This is in complete agreement with the knowledge that when transplanting tissue the greatest success is achieved when the tissue graft has been cooled during the process. By cooling and consequent reduced metabolism, the life time of the tissue is thus increased.

Over the last few decades occlusive treatment of wounds has been increasingly used, and everything indicates that within not too long a time occlusive treatment of various kinds of wounds, such as burns, operative wounds, bed sores, leg sores, and diabetic wounds, will be the most commonly used method of treatment.

The great success of the occlusive method of treatment is largely due to the moist wound environment, which a number of examinations have shown i.a. causes an increased migration of epithelial cells. More recent experiments have, however, shown that the isolating effect of the occlusive method of treatment also plays an important part for the wound-healing. By occlusive treatment, the treated skin and wound areas are isolated, which may result in a slight increase in the surface temperature of the skin and wound areas. Thus, it is not an active heating, but only a shielding, whereby the heat loss from the surface of the skin and wound areas is minimized.

In spite of the fact that there is thus an indication that the temperature in a wounded skin area has significant influence on the healing process, and that by raising the temperature it is possible to increase the speed of healing, use of sustained heat for local treatment of wounds has as far as known not yet been used in practice.

For such nuisances in body and skin areas which it is known to treat with heat, the heat is usually applied by heat ray impact. It is often a matter of heat treatment of larger body and skin areas, but also local heat treatment is performed by means of heat rays.

Treatment with heat rays can, however, only be performed within the framework of hospitals or clinics, and is furthermore very expensive both as regards equipment and staff costs.

Usually the heat treatment must be performed several hours daily to obtain an efficacious effect. In particular when treating rheumatism and, which has been found at a later date, when treating wounds, a continuous treatment is required.

Thus, it is not only very expensive but also exacting on the patients' patience each day to have to go through hours of treatment with heat rays.

Another commonly known method of heat treatment is treatment with heat bags or heat pads. This mode of treatment is used in particular for minor nuisances, and the treatment is most frequently prescribed by the patient himself.

Heat pads generally consist of a pad of synthetic material with inlaid electric resistors in which the heat is generated by connection to the mains. Heat pads are used most frequently for menstrual pain and for milder forms of rheumatism. By treatment with heat pad, the patient, as in the case of treatment with radiation heat, is forced to sit or lie still for the duration of the treatment.

Heat bags may also be electrically heated, but most often they are chemically heated. The chemically heated heat bags consist of an oxygen-permeable bag containing a metal powder which oxidizes upon contact with oxygen, whereby heat is generated. Generally, metals, such as iron, aluminium or magnesium, are used, and in particular in the form of porous powders. The metal powders are usually mixed with catalysts and assistants, such as chloride ions and active carbon, as well as fillers and moisteners, such as bentonite and cellulose compounds. Heat bags of this kind are well known, and further mention hereof can be found e.g. in U.S. Pat. Nos. 4,282,005, 4,268,272, 4,106,478, 4,516,564, and 3,976,046, and in DE public disclosure No. 3 404 654 and DE patent specification No. 3 649 115.

The existing heat bags of the above type are especially used for treatment of infiltrations and sports injuries and as heat aggregate for people staying outdoors for quite a long time.

The heat bags are not particularly well-suited for use directly against the skin, since the heat development can be difficult to control. The skin is very heat-sensitive. Experiments with local heating of the skin have thus shown that heating of a skin surface area of 1 cm$^2$ to a temperature of above 43° C. for a prolonged period can cause severe burns. The temperature is especially critical in skin areas with impaired blood flow. The skin temperature is by treatment with a heat bag furthermore dependent not only on the amount of heat supplied, but also on the skin's own temperature, blood flows in the skin area, and the temperature of the surroundings.

Some of the known chemically heat generating heat bags are shaped as plane dressings which essentially have the same thickness throughout the entire extension of the dressing. This somewhat alleviates the problem, since the heat generating metal powder in such a heat dressing is evenly distributed over the entire area of the dressing.

By futher control of the air supply, chemically heat generating dressings have thus been achieved which in one surface area of the entire heat dressing essentially gives off a uniform amount of heat.

In spite of a uniform heat emission, a heat dressing placed directly against the skin can all the same give rise to local superheating, and consequently burns on the skin.

As mentioned above there are several factors influencing the skin's surface temperature by treatment with a heat dressing.

A particularly significant factor is the condition of the skin, and in particular the blood flow in the areas is of great importance.

A heat dressing having a surface area of e.g. 100 cm$^2$ will thus cover skin areas with essential differences in blood flow. In the very local areas with a low blood flow, a heat agglomeration can thus easily occur, so that the temperature in these areas exceeds the average contact temperature of the heat dressing.

Patients with rheumatism are mostly older people whose blood flow, in particular in the outer skin layers, is impaired. Similarly, the blood flow in wounded skin areas, in particular in case of leg sores, is often considerably reduced.

When treating such patients with a heat dressing, there is thus a particularly large risk of local superheating of the skin, and consequently risk of burns.

Another essential cause for local superheating is the poor or defective contact between the heat dressing and the treated skin surface, in particular if the treated surface is essentially curved.

If the heat dressing is only in contact with the skin surface in part of the surface area of the dressing, the heat is essentially transferred to the skin surface area which is in contact. Since the heat given off from the dressing is independent of the contact area of the dressing, the skin surface area which is in contact will be supplied with more heat than intended, whereby the area easily becomes superheated.

In a treatment with a heat dressing, the dressing is usually placed "loosely" on the area of treatment, which causes the patient great nuisance since he must necessarily sit of lie still for the duration of the heat treatment.

However, a few dressings are known which can be attached by means of attaching bands. These dressings, however, can only be used for treatment of skin areas on arms and legs, and furthermore the attachment is not very stable, and the dressing is very liable to get displaced or fall off completely when the patient moves.

EP patent application No. 376 490 discloses a heat dressing consisting of a flat bag containing iron powder and water retaining agents. One of the bag sides is air-permeable, and the other bag side is provided with a thin layer of an acrylic adhesive which enables the heat dressing to be attached to clothing or directly to the skin surface.

Acrylic adhesives are normally considered skin-friendly adhesives and are widely used for plasters and microporous tapes which are moisture-penetrable. Heat dressings of the above type have, however, been found to cause significant skin nuisances when placed directly on the skin.

The heat dressing with acrylic adhesive causes in particular substantial skin irritation in the form of itching, smarting, and prickling in the skin surface, but by use of a heat dressing provided with acrylic adhesive directly on the skin also pronounced maceration, increased bacterial and fungal growth, and considerable changes in the skin's pH-value will be noted.

As mentioned above, the heating of the skin causes significant changes in the metabolic processes of the skin tissue. The changes i.a. cause increased excretion of liquid and waste substances through the skin, and the skin's sensitivity to exogenous impacts is generally increased.

These factors presumably are the reason why positioning of the dressing known from the EP patent application directly on the skin causes the above skin nuisances.

DE public disclosure No. 3 434 292 discloses another self-adhesive heat dressing which either on the entire surface facing the skin or in an edge area is coated with an adhesive. However, nothing is said about which adhesives may be used, and further it is stated as patentable measure that the surface facing the skin is coated with an analgesic. This analgesic may give further rise to the patient getting burnt by the dressing, since the patient, because of the skin's nerve endings being "unconscious" will not react as quickly in case of a local superheating.

SUMMARY OF THE INVENTION

The object of the present invention is to devise a self-adhesive heat dressing which does not suffer from the disadvantages described above, and which thus essentially does not cause skin irritation, increased bacterial or fungal growth or significant changes in the skin's pH-value.

The above object is achieved by the heat dressing according to the invention which is of the kind, and which is characterized by the adhesive material being liquid-absorbing.

DESCRIPTION OF THE INVENTION

It has thus surprisingly been found that a heat dressing which is provided with a liquid absorbing adhesive in spite of the changed metabolism of the skin tissue caused by the heat treatment does not give rise to skin irritation and is further capable of preventing an increased bacterial or fungal growth, as well as significant changes in the skin's pH-value.

Furthermore it has surprisingly been found that the heat dressing according to the invention entails reduced risk of local superheating and thereby reduced risk of burns on the skin surface, since it has been found that liquid-absorbing adhesives have an excellent heat distributing capacity, whereby local heat agglomerations are avoided, and at the same time maceration of the skin is essentially avoided.

It has further been found that the heat dressing according to the invention by use for treatment of skin areas with reduced blood flow, such as wounded skin areas, in particular leg sores and skin areas on older people, in particular rheumatic patients, has attained surprisingly good results.

The heat dressing according to the invention comprises, as mentioned above, a preferably flat heat generating unit, one side surface of which is coated with a liquid-absorbing adhesive, which furthermore prior to use is coated with a strippable adhesive layer.

The heat generating unit is capable of generating heat in any suitable way. The heat can e.g. be generated by galvanic energy, where electrically conducting foil or hot wires are inlaid in the unit in an area-wise suitable embodiment, and where the energy is supplied from batteries or from the mains via a transformer. The hot wires or the conducting foil may suitably be shielded from any wound exudate e.g. by being laminated between two plastic films. Furthermore, it is possible e.g. by means of a control circuit, optionally with thermistor, to build in an effect/temperature control so that an optimum temperature can be observed.

Another extremely suited method of generating heat is oxidation of metal powder, which has been mentioned earlier in the description.

Examples of other suited heat generating methods especially include utilization of crystallization heat, decomposition heat, sulphide oxidation, and reaction heat from cements.

The adhesive layer may be any liquid absorbing adhesive, e.g. a hydrocolloidal adhesive or a hydrogel adhesive.

Hydrogel adhesives consist of a liquid-absorbing cross-linked polymer, such as collagen, polyvinylalcohol, polyacrylate and gelatine.

A hydrogel adhesive contains a large amount of water already before it is used. In such cases where the adhesive is substantially water-saturated, the adhesive is usually only negligently self-adhesive, and must therefore be used in combination with another adhesive, which is explained in more detail later in the description. Other hydrogel adhesives with lower water content exhibit excellent adhesive properties. Certain modified gellable polymers are, however, capable of retaining a fairly good adhesive capacity, even when essentially being water-saturated.

Hydrogel adhesives are described in e.g. EP public disclosure No. 97846 and No. 415183, SE published application No. 365 410, WO public disclosure No. 88/6894 and U.S. Pat. No. 4,093,673.

Hydrocolloidal adhesives normally consist of (i) a continuous phase containing an adhesive and e.g. being built from an elastomer, an emollient for elastomers, a resin promoting the adhesive capacity, and optionally an oil-based extender, as well as an antioxidant, and (ii) a discontinuous phase dispersed therein comprising one or more water-soluble or water-swellable hydrocolloids, such as starch derivatives or cellulose derivatives, or other hydrophilic polymers.

Such adhesive materials are e.g. known from DK patent specifications No. 147 034 and No. 147 035 (corresponding to U.S. Pat. Nos. 4,231,369 and 4,367,632). The adhesive materials herein mentioned consist of (I) a continuous phase comprising
   (a) a physically cross-linked elastomer in the form of one or more styrene-olefine-styrene block copolymers or ethylene-propylene block copolymers,
   (b) a hydrocarbon tackifier in the form of a polymer or copolymer from cyclopentadiene, dicyclopentadiene, α-pinene and/or β-pinene,
   (c) an antioxidant,
   (d) optionally an oil extender in the form of one or more mineral oils, and
   (e) a polar emollient for the elastomer, such as e.g. an ester of a polyethyleneglycol or polypropyleneglycol, or an ester of a di- or polybasic carboxylic acid with a preferably aliphatic alcohol, and (II) a phase dispersed in the continuous phase comprising one or more water-swellable hydrocolloids.

Known liquid-absorbing adhesive materials may also contain other elastomers, e.g. natural rubber, synthetic resins of similar nature as natural rubber and silicone rubbers. As structure-forming component in adhesive materials, use is also frequently made of polyisobutylene of a suitable molecular weight distribution, e.g. as stated in U.S. Pat. No. 3,339,546.

Other adhesive materials of similar nature are known e.g. from NO published application No. 157 686, U.S. Pat. No. 4,867,748, and DK patent specifications No. 154 806, No. 147 226, No. 157 899 and No. 154 747.

The adhesive material may further contain various medicaments, since the heat dressing according to the invention has proved to be extremely well-suited as transcutaneous dosing agent for dosing various medicaments, such as hormones or nicotine.

Adhesive materials containing such medicaments have already been mentioned in several of the above patent publications.

The adhesive layer may consist of two or more different adhesives positioned in a pattern next to each other, in the way it is known from DK published application No. 157 899. A low-adhering hydrogel adhesive may very well be used in such a combination.

The adhesive layer may further be coated centrally with one or more alginate fibre mats. Such a heat dressing according to the invention with an alginate coated adhesive layer is primarily intended for treatment of exudating wounds, and in use it must be ensured that the alginate fibre mat does not have an extension which is significantly larger than the wound area, since the alginate coated skin area, if the alginate mat is dry, is not in optimum contact with the heat dressing.

If in doubt whether the wound exudates sufficiently to cause rapid moistening of the alginate mat, it is advisable to moisten the mat by dripping thereon a sterile liquid prior to application of the heat dressing.

To achieve good liquid capacity and good heat distribution capacity, the adhesive layer must not be too thin. On the other hand the adhesive layer must not be too thick either, since a certain flexibility of the heat dressing is particularly advantageous, especially when using the dressing on very curved skin surfaces.

Thus the adhesive layer should preferably have a thickness of more than 0.25 mm, and in particular between 0.5 and 2.0 mm.

The heat dressing according to the invention may furthermore on its outer side (the side facing away from the skin) be provided with a heat-reflecting foil, whereby the heat loss to the surroundings may be reduced to a minimum.

Further, the heat dressing according to the invention may on its outer side be provided with a layer of a polymeric foam. Such a foam layer has both heat-insulating and pressure-alleviating effects.

If the dressing according to the invention requires supply of air for heat generation, it is in case of the last-mentioned measures of course necessary to ensure that such air supply is not hampered.

According to a special embodiment of the heat dressing according to the invention, a liquid barrier is provided between the heat generating unit and the liquid-absorbing adhesive layer. This liquid barrier may e.g. be constituted by the inner side of the heat generating unit, or a liquid-impermeable film may be positioned between the liquid-absorbing adhesive layer and the heat generating unit, which film is attached to the heat generating unit by a secondary liquid-absorbing of non-liquid-absorbing adhesive.

In this special embodiment of the heat dressing according to the invention, the adhesive layer and the liquid-impermeable film may have a larger surface area than the heat generating unit, so that the adhesive and the liquid-impermeable film in the edge area of the heat dressing are not in contact with the heat generating unit. Heat dressings according to the invention of this type may suitably have bevelled edges as known from DK published application No. 154 747.

The heat dressing according to the invention may further be so shaped that the heat generating unit is replaceable, the adhesive part consisting of an adhesive layer and a liquid-impermeable film on its film side being provided with a coupling means which is capable of retaining the heat generating unit in close contact with the adhesive part for any desired duration. The coupling means may e.g. by a film sheet being attached to the film side of the adhesive part along three of its edges, so that the heat generating unit may be introduced at the fourth and open edge and retained in close contact with the adhesive part of the film sheet. If the heat generating unit generates heat by chemical energy, it is preferred that the film sheet is perforated.

Before use the heat dressing according to the invention has on its adhesive side been provided with a strippable cover layer.

If the heat dressing according to the invention generates its heat by reaction with oxygen in the air, it must prior to use be packed in an air-tight, non-oxygenous package. One of the inner surfaces of this package may well constitute a strippable cover layer facing the adhesive side.

BRIEF DESCRIPTION OF THE DRAWINGS

In the following, the invention is described in more detail, reference being made to the drawings and the examples, in which.

DETAILED DESCRIPTION OF THE DRAWING

Figure 1:
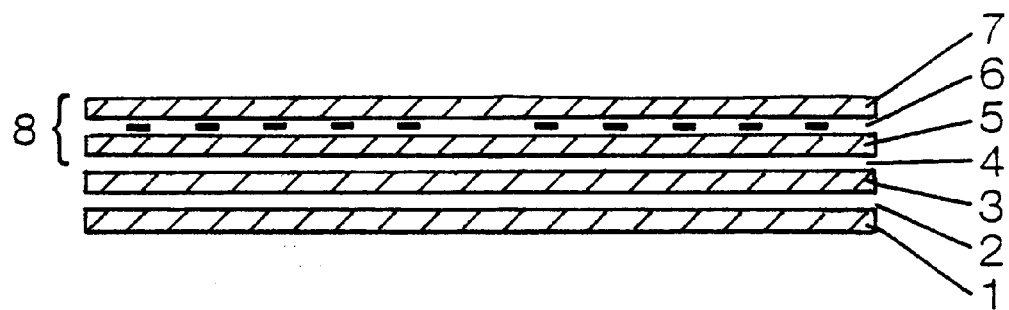
FIG. 1 is a side-view of an embodiment of the heat dressing, the dressing being intersected at AA' (FIG. 2).
Figure 2:
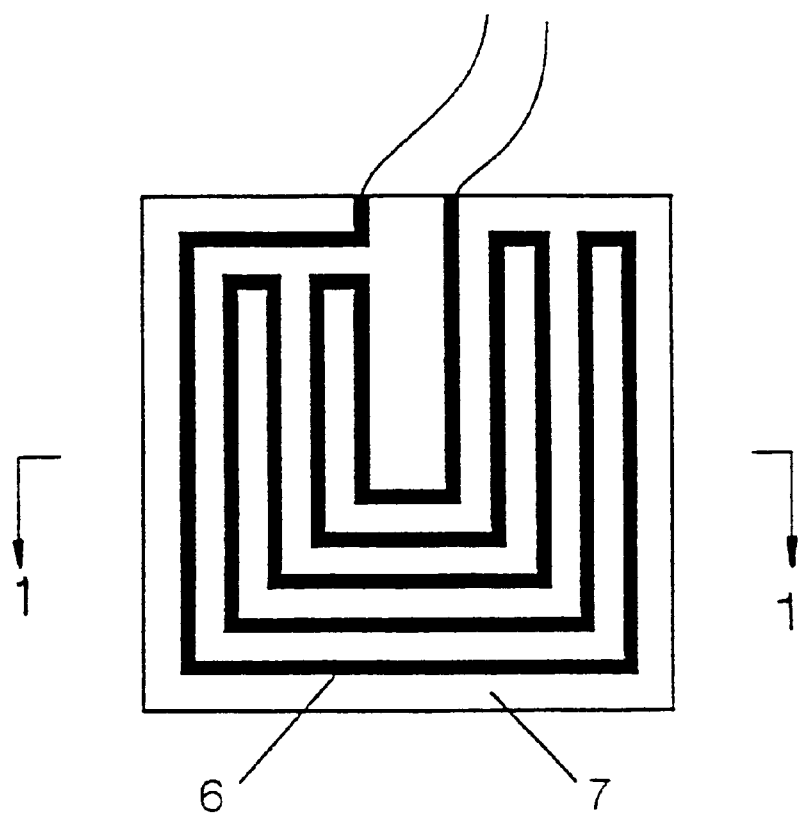
FIG. 2 is a top view of the dressing shown in FIG. 1.

The heat dressing according to the invention shown in FIGS. 1 and 2 consists of a liquid-absorbing adhesive layer (2), preferably a hydrocolloidal adhesive layer, which is coated with a strippable release layer (1), e.g. a paper layer, being surface treated with silicone. On its othe side the adhesive layer (2) is coated with a liquid-impermeable film (3) consisting of e.g. polyurethane, polyethylene, polybutadiene, polyvinylchloride, polyvinylidenechloride, polyvinylalcohol, polyacrylate, polysulphon, polystyrene, polypropylene, polyamide, ethylene-vinylacetate-copolymer, polyester, polycarbonate, polyvinylfluoride, copolyesterether, synthetic rubbers, silicone, and mixtures thereof. Elastomers, such as polyurethane, polyester, copolyesterether and synthetic rubbers, are particularly preferred.

The film layer may further contain various additives, such as anti-blocking agent, e.g. $SiO_2$ and talc powder, emollients, e.g. dioctyladipate, and fillers and pigments.

A heat generating unit (8) is fixedly adhered on top of the film layer by means of an adhesive layer (4). The adhesive layer (4) may consist of any adhesive having a reasonable heat conducting capacity and a reasonable adhesive capacity.

The heat generating unit (8) consists of a conducting foil-string (6), preferably aluminium foil. For the sake of clarity the conducting foil-string (6) is in FIG. 2 sketched so that there are comparatively large spacings. The foil-string (6) may, if desired, lie closer, since the position and closeness of the strings (6) are chosen so that the surface of the heat dressing facing the skin essentially gives off a uniform amount of heat across the entire area of the surface.

The foil-string (6) is at either end connected to a conducting wire. The two conducting wires are insulated and are connectable to an energy source, such as a battery or the mains via transformer, with a not shown thermostat-controlling unit, such as a control circuit with PTC-thermistor, optionally being connected.

The foil-string (6) and the PTC-thermistor are encased by a film layer (5,7) of e.g. polyurethane, polyethylene, polybutadiene, polyvinylchloride, polyvinylidenechloride, polyvinylalcohol, polyacrylate, polysulphon, polystyrene, polypropylene, polyamide, ethylene-vinylacetate-copolymer, polyester, polycarbonate, polyvinylfluoride, copolyesterether, synthetic rubbers, silicone, and mixtures thereof. Elastomers, such as polyurethane, polyester, copolyesterether and synthetic rubbers, are particularly preferred.

Further, the upper film layer (7) may suitably consist of or be coated with a heat-reflecting material. The film layer (7) shown in FIG. 2 is of a transparent material.

The two film layers (5,7) may be welded, fused or otherwise secured to each other.

Figure 3A:
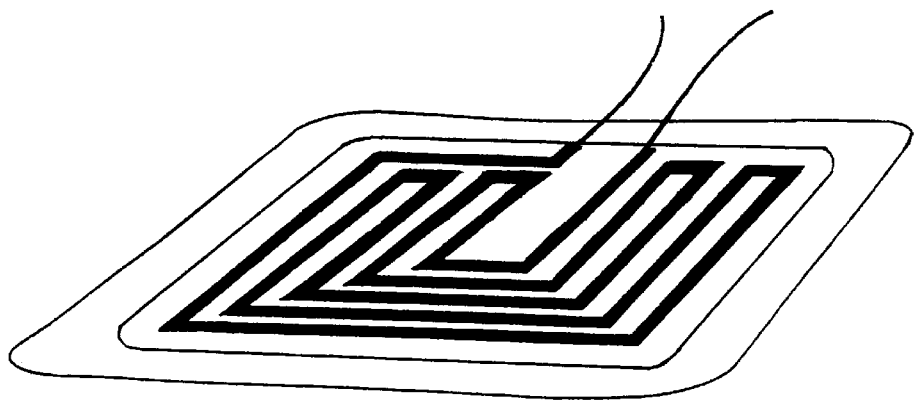
FIG. 3a is a variant of the dressing shown in FIGS. 1 and 2.
Figure 3B:
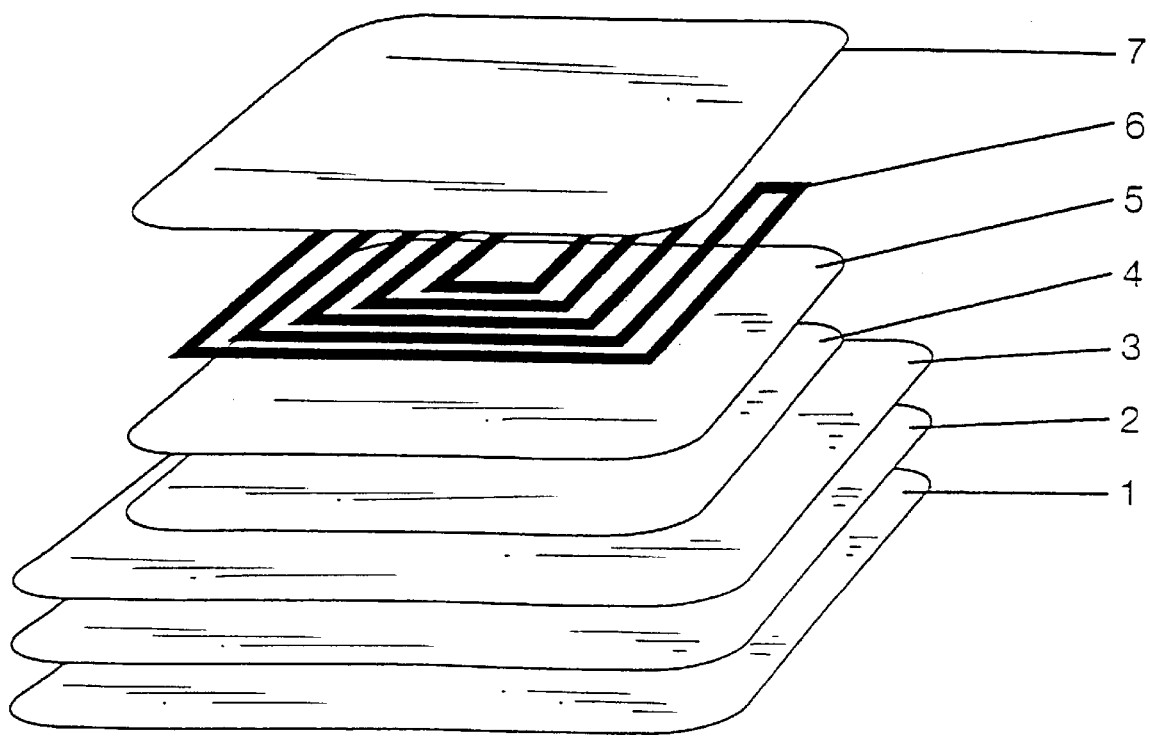
FIG. 3b is the dressing shown in FIG. 3a in exploded state.

The heat dressing shown in FIGS. 3a and 3b is a variant of the heat dressing according to the invention shown in FIGS. 1 and 2.

The adhesive layer (2) with the strippable release layer (1) and the liquid-impermeable film (3) has a larger surface extension than the heat generating unit which consists of a conducting foil-string (6) being coated with an upper and a lower film layer (7,5). The adhesive part and the heat generating part are intersecured by an adhesive layer (4) which has the same extension area-wise as the heat generating part.

Figure 4:
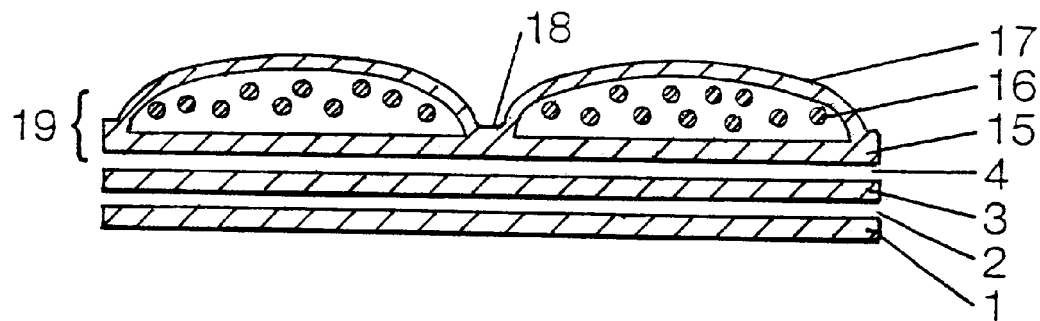
FIG. 4 is a side view of another embodiment of the heat dressing according to the invention, the dressing being intersected at BB' (FIG. 5).
Figure 5:
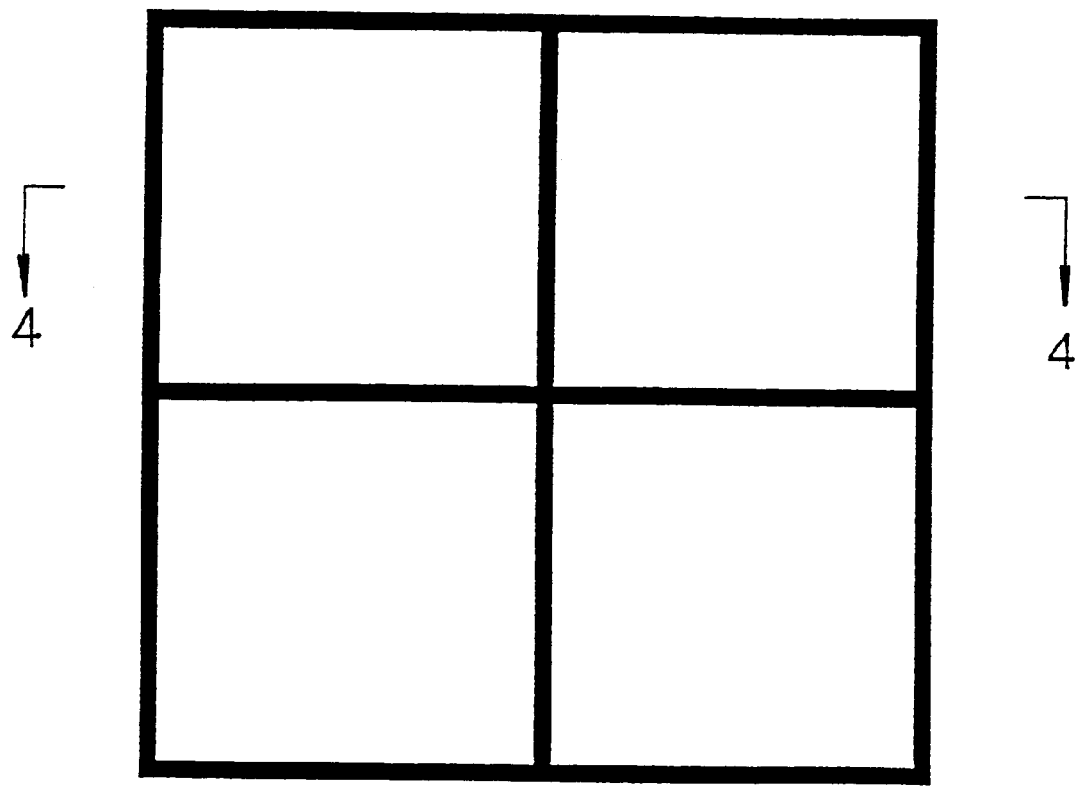
FIG. 5 is a top view of the dressing shown in FIG. 4.

FIGS. 4 and 5 show a heat dressing according to the invention which is heated by chemical energy. The adhesive layer (2), the strippable cover layer (1) and the liquid-impermeable film (3) correspond to like parts of the heat dressing according to the invention shown in FIGS. 1–3.

The heat generating unit (19) consists of a first film layer (15) which is attached to the liquid-impermeable film (3) by means of a thin adhesive layer (4), and a second film layer (17) which along the periphery of the heat unit and in two welding lines (18) progressing transversely to the heat unit (19) is attached to the film (15), so that the heat generating unit (19) is divided into four bag sections containing metal powder (16) which by reaction with the oxygen in the air is oxidized, whereby heat is developed. The film layer (17) is suitably permeable for the oxygen in the air, e.g. by perforations in the film layer (17). The two film layers (15, 17) may e.g. be selected from the same materials which by way of example are stated for the films (3, 5, 7) in FIGS. 1–3. The reaction speed is further adjusted by admixing various additives in the metal powder, which has been discussed earlier in the description.

EXAMPLE 1

A comparative examination of the wound-healing speed of leg sores was performed using a non heat generating occlusive dressing and a heat dressing according to the invention, respectively.

Dressing A

Comfeel® Ulcer Dressing, 10×10 $cm^2$ having a thickness of approx. 1.1 mm (marketed by Coloplast A/S).

Dressing B

Comfeel® Ulcer Dressing, 10×10 $cm^2$ having a thickness of approx. 2.1 mm and on the film side of which a heat unit had been attached by means of Micropore® tape (marketed by 3M) along the edges of the heat unit. The heat unit was positioned centrally on the film, and its size was 5×5 cm², and its capacity 15 mW/cm² (equiv of Δ3.5° C.).

Two groups of 5 patients with venous leg wounds were selected and treated with dressing A and dressing B, respectively.

Comprilan® compress was used identically in both groups, which as far as possible were quite comparable.

The dressings were changed 2–3 times a week, and the treatments lasted for 3 weeks.

In the group which was treated with dressing B, an average weekly area reduction of the wound of 15.3% was achieved as compared with the control group of 7.2% over a period of 3 weeks. It was thus evaluated that local heat supply via a dressing according to the invention has a considerable healing-promoting effect on chronic leg sores.

EXAMPLE 2

A patient having a large venous leg sore (55 cm²) was treated with a heat dressing on one part of the wound to be controlled against the other part.

In the experiment, the wound was by means of a vertically placed brim of hydrocolloidal wound pasta (Comfeel® Pasta) divided into in two equally large sections.

An experimental hydrogel wound dressing CP-DN19 was produced, which consisted of a PVAL/PVP copolymer with a top film of polyurethane (thickness 30 $\mu$m), the size of its area being 10×10 cm², and a heat unit having a surface area of 2×8 and being supplied with a DC-voltage corresponding to an effect of 20 mW/cm², which by means of Micropore® tape was attached to the top film.

The heat unit was attached to the top film at a distance of 1 cm from three of the edge sides of the dressings and at a distance of 6 cm from the fourth edge side. A line was drawn at a distance of 5 cm from the fourth edge side, so that the dressing was divided into two halves, viz. half A without heat unit and half B with heat unit.

The CP-DN19 dressing was placed over the entire wound including pasta brim, so that the centre line precisely covered the pasta brim. The CP-DN19 dressing was coated with a Comprilan® compress. The treatment lasted for 14 days, during which the wound was attended to regularly.

Granulation tissue formation was noted after 2–3 days on the part of the wound which was covered by dressing half B, and not until after approx. 10 days on the part of the wound which was covered by dressing half A.

After 14 days, the wound area under dressing half B had been reduced by 28% versus merely 8% under dressing half A.

EXAMPLE 3

A heat dressing according to the invention was compared with a heat dressing without liquid-absorbing properties, changes in the skin's pH-value and Trans Epidermal Water Loss (TEWL) being observed.
Dressing A
This non-absorbing dressing consisted of a 60 $\mu$m thick saffron film, coated with a 30 $\mu$m thick layer of self-adhesive polyvinylether on one side and a heat dressing on the other.
Dressing B
This absorbing dressing consisted of DuoDerm® having a thickness of approx. 2.1 $\mu$m (marketed by Convatec), a heat unit being mounted on its film side.

Both dressings had an extension area-wise of 10×10 cm², of which the heat unit centrally covered an area of 5×5 cm², being attached along its edge sides by Micropore® tape. The heat unit had for both dressings an effect of 10 mW/cm².

After 72 hours, skin pH and TEWL were analyzed by standard methods.

| Dressing | pH | g/m²/h TEWL |
|---|---|---|
| B | 4.8 ± 0.6 | 7.2 ± 2.1 |
| A | 7.8 ± 0.8 | 21 ± 7 |

The absorbing dressing thus prevents moistening of the skin and shift in pH (normal 5–6).

The experiment further showed that the volunteers for the test complained of spot-wise strong heat and discomfort under the non-absorbing dressing.

EXAMPLE 4

A heat dressing according to the invention was compared with a heat dressing without liquid-absorbing properties by experiments on rats.
Dressing A
This non-absorbing dressing consisted of an OpSite® dressing having a thickness of about 60 $\mu$m, a heat unit being positioned on its film side.
Dressing B
This dressing according to the invention consisted of a Comfeel® Ulcer Dressing having a thickness of about 1.1 mm, a heat unit being positioned on its film side.

Both dressings had a size of 2×6 cm, and the heat unit was centrally positioned and covered an area of 1×4, and being, as in the previous examples, attached by Micropore® tape. The heat units had an effect of 15 mW/cm².

Two groups of 6 rats were wounded on their backs, and group 1 was treated with dressing A, and group 2 was treated with dressing B.

The treatment lasted for 10 days without change of dressing, whereafter the test animals were killed and the healing ascertained.

A significant difference in healing-speed between the two groups was noted, wound size in % of initial wound excission being determined at 11%±6 in rat group 1, and 29%±6 in rat group 2.

It is thus quite clear that dressing B according to the invention results in a far quicker wound-healing than dressing A.

We claim:

1. A heat dressing comprising a substantially planar heat generating unit being coated on one side surface thereof with a layer of liquid absorbing adhesive material comprising a hydrogel or hydrocolloid which prior to use of the dressing is coated with a strippable cover layer, said heat generating unit generating heat by means of electrical energy.

2. A heat dressing according to claim 1, characterized in that the adhesive material is a hydrocolloidal adhesive.

3. A heat dressing according to claim 2, characterized in that the adhesive layer has a thickness in excess of 0.25 mm.

4. A heat dressing according to claim 3, characterized in that the adhesive layer has a thickness between 0.5 and 2.0 mm.

5. A heat dressing according to claim 1, characterized in that the adhesive material consists of two or more different liquid-absorbing adhesive materials which are positioned next to each other.

6. A heat dressing according to claim 3, characterized in that one of the adhesive materials is a low adhesive strength hydrogel adhesive.

7. A heat dressing according to claim 1, characterized in having one or more alginate fibre mats centrally positioned on a surface of the adhesive.

8. A heat dressing according to claim 1, characterized in that the adhesive layer has a thickness in excess of 0.25 mm.

9. A heat dressing according to claim 8, characterized in that the adhesive layer has a thickness between 0.5 and 2.0 mm.

10. A heat dressing according to claim 1, characterized in that the liquid-absorbing adhesive material contains one or more medicaments.

11. A heat dressing according to claim 1, characterized in that the heat generating unit comprises a conducting element selected from the group consisting of conducting foil and conducting wires.

12. A heat dressing according to claim 11, characterized in that the foil or the wires are laminated between two plastic films, and that the heat generating unit further comprises a control circuit.

13. A heat dressing according to claim 12, characterized in that the control circuit comprises a thermistor.

* * * * *